US012642788B2

(12) United States Patent
Cheon et al.

(10) Patent No.: US 12,642,788 B2
(45) Date of Patent: Jun. 2, 2026

(54) PHARMACEUTICAL COMPOSITION COMPRISING BENZIMIDAZOLE DERIVATIVE COMPOUND

(71) Applicant: HK INNO.N CORPORATION, Cheongju-si (KR)

(72) Inventors: Jae Hee Cheon, Seoul (KR); Seung Won Kim, Seoul (KR); Mi Jeong Son, Busan (KR); I Seul Park, Gyeonggi-do (KR); Dongkyu Kim, Gyeonggi-do (KR); Bong Tae Kim, Gyeonggi-do (KR); Eun Ji Kim, Seoul (KR); Jae Yong Han, Seoul (KR)

(73) Assignee: HK INNO.N CORPORATION, Chungcheongbuk-do (KR)

( * ) Notice: Subject to any disclaimer, the term of this patent is extended or adjusted under 35 U.S.C. 154(b) by 587 days.

(21) Appl. No.: 18/009,060

(22) PCT Filed: Oct. 30, 2020

(86) PCT No.: PCT/KR2020/015099

§ 371 (c)(1),
(2) Date: Dec. 8, 2022

(87) PCT Pub. No.: WO2021/251565

PCT Pub. Date: Dec. 16, 2021

(65) Prior Publication Data

US 2023/0248703 A1 Aug. 10, 2023

(30) Foreign Application Priority Data

Jun. 12, 2020 (KR) ........................ 10-2020-0071909

(51) Int. Cl.
*A61K 31/4184* (2006.01)
*A61K 9/00* (2006.01)
*A61P 1/00* (2006.01)

(52) U.S. Cl.
CPC ........ *A61K 31/4184* (2013.01); *A61K 9/0053* (2013.01); *A61P 1/00* (2018.01)

(58) Field of Classification Search
CPC .............................. A61K 31/4184; A61P 1/00
See application file for complete search history.

(56) References Cited

U.S. PATENT DOCUMENTS

2017/0258867 A1 9/2017 Kåss

FOREIGN PATENT DOCUMENTS

| | | | |
|---|---|---|---|
| KR | 10-2016-0104730 | A | 9/2016 |
| KR | 10-1829706 | B1 | 2/2018 |
| WO | WO2016200148 | A1 | 12/2016 |

OTHER PUBLICATIONS

Son et al., "Anti-inflammatory Effect of Tegoprazan (CJ-12420), A Novel Potassium-Competitive Acid Blocker, In DSS-Induced Colitis Mouse Model", Gastroenterology, vol. 158, No.6, Suppl. 1, pp. S276-S277, Abstract No. Sa1103 (May 2020).*

Kim, Dong Kyu et al., 'Effects of tegoprazan, a novel potassium-competitive acid blocker, on rat models of gastric acid-related disease', The Journal of Pharmacology and Experimental Therapeutics, Jun. 2019, vol. 369, No. 3, pp. 318-327.

Takahashi, Nobuyuki et al., 'Tegoprazan, a novel potassium-competitive acid blocker to control gastric acid secretion and motility', The Journal of Pharmacology and Experimental Therapeutics, Feb. 2018, vol. 364, No. 2, pp. 275-286.

Digestive Disease Week (DDW) ePoster (Online Poster), Anti-Inflammatory Effect of Tegoprazan (CJ-12420), a Novel Potassium-Competitive Acid Blocker, in DSS-Induced Colitis Mouse Model, May 2, 2020.

International Search Report and Written Opinion for PCT/KR2020/015099, International Searching Authority—Korean Intellectual Property Office, Mar. 11, 2021.

Kedika et al., "Potential Anti-Inflammatory Effects of Proton Pump Inhibitors: a Review and Discussion of the Clinical Implications," Dig Dis Sci. Nov. 2009; 54 (11): 2312-2317; doi:10.1007/s10620-009-0951-9.

"Omeprazole in ulcerative colitis," The Lancet, vol. 343, Feb. 19, 1994.

* cited by examiner

*Primary Examiner* — Kevin E Weddington
(74) *Attorney, Agent, or Firm* — Giordano Law LLC; David A. Giordano

(57) ABSTRACT

The present invention provides a pharmaceutical composition for preventing or treating colitis comprising tegoprazan, which is a benzimidazole derivative compound, as an effective ingredient.

14 Claims, 8 Drawing Sheets

[Fig. 1]
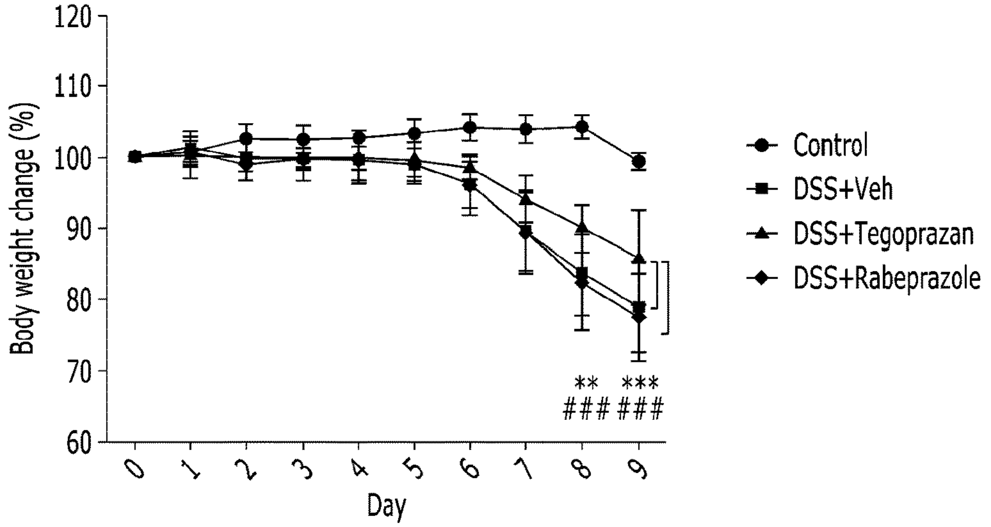
[Fig. 2]
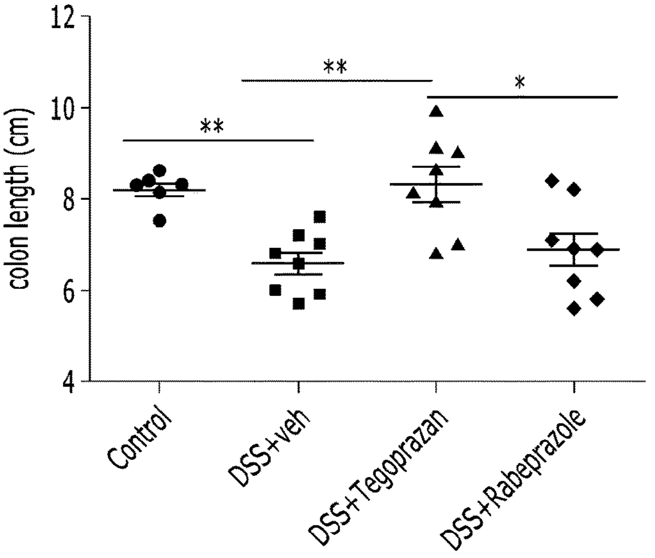
[Fig. 3]
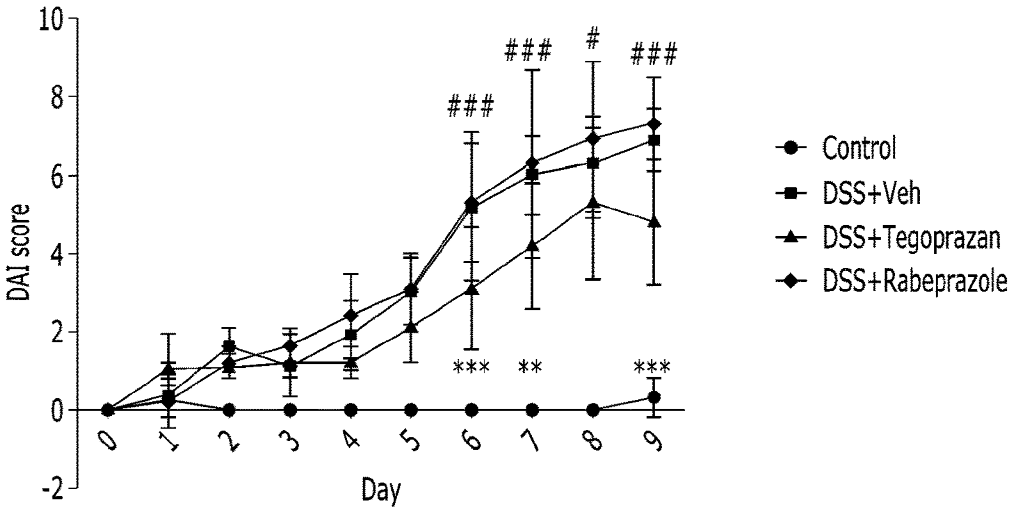

[Fig. 4]
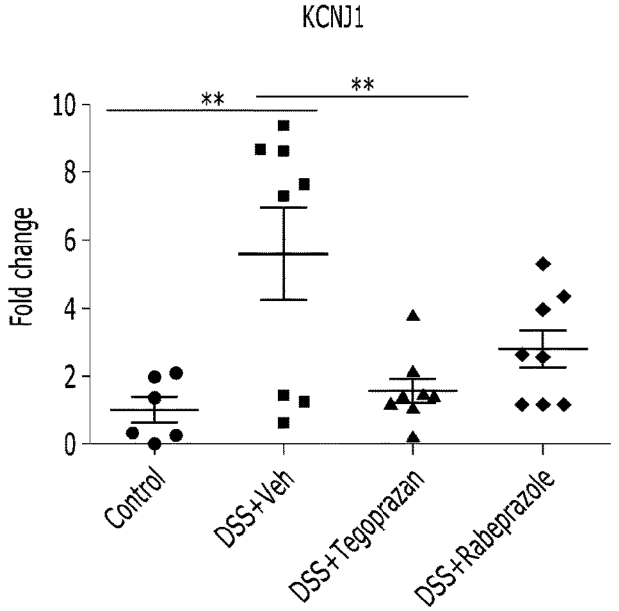
[Fig. 5]
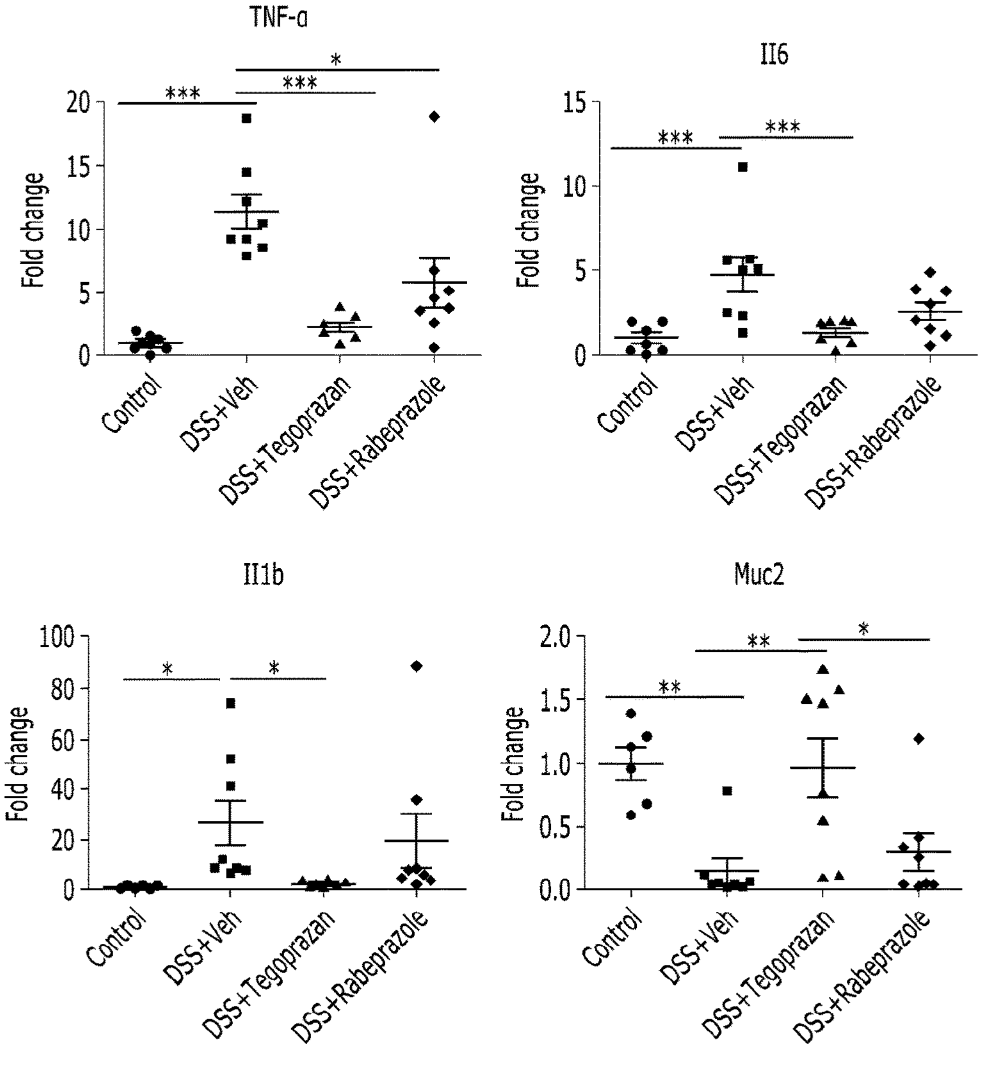

[Fig. 6]
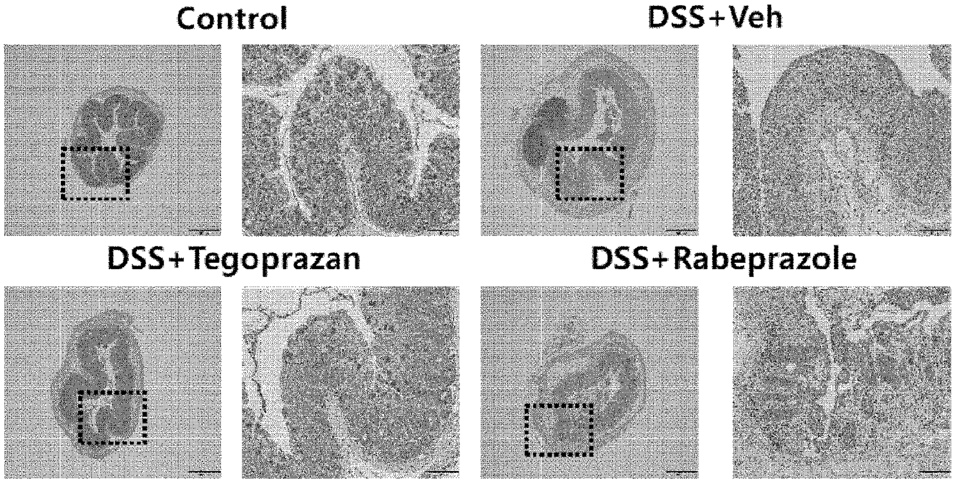
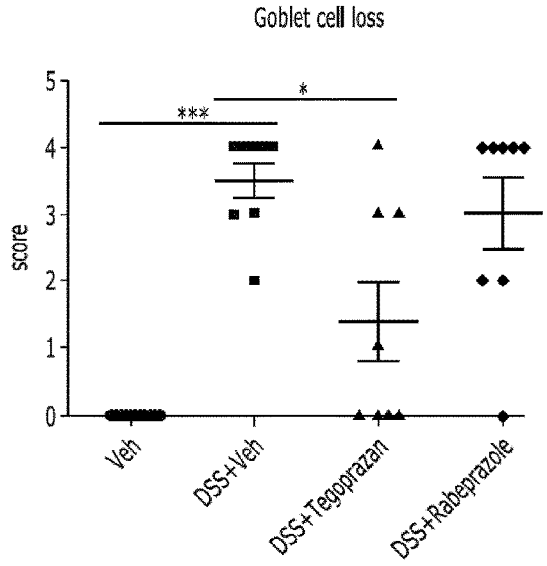
[Fig. 7]
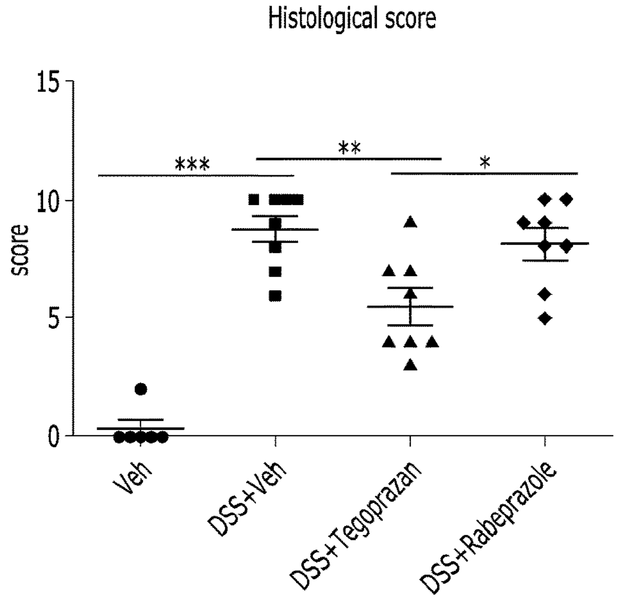

[Fig. 8]
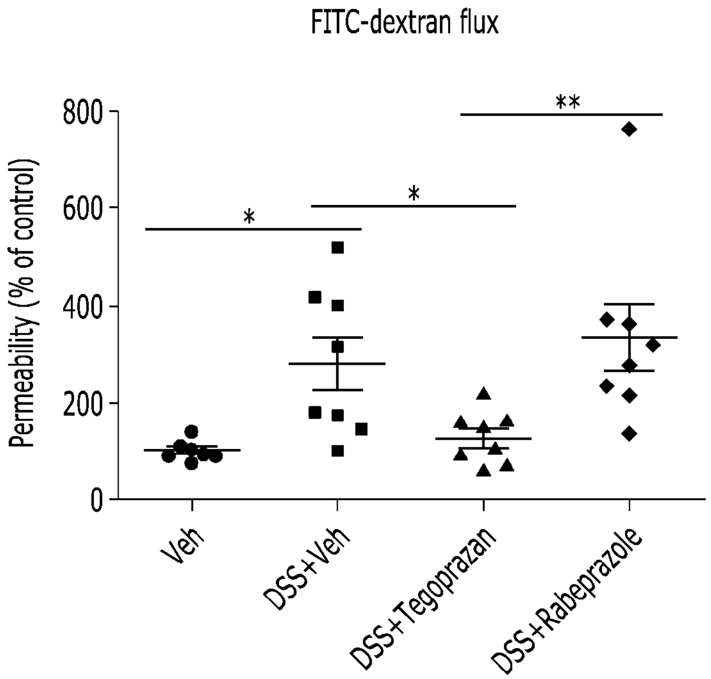
[Fig. 9]
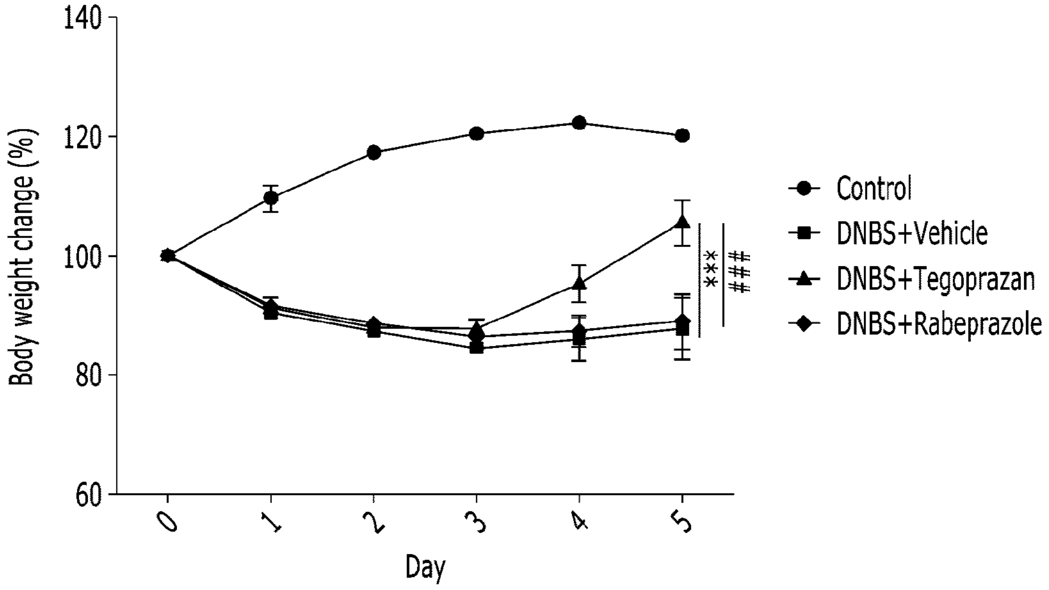

[Fig. 10]
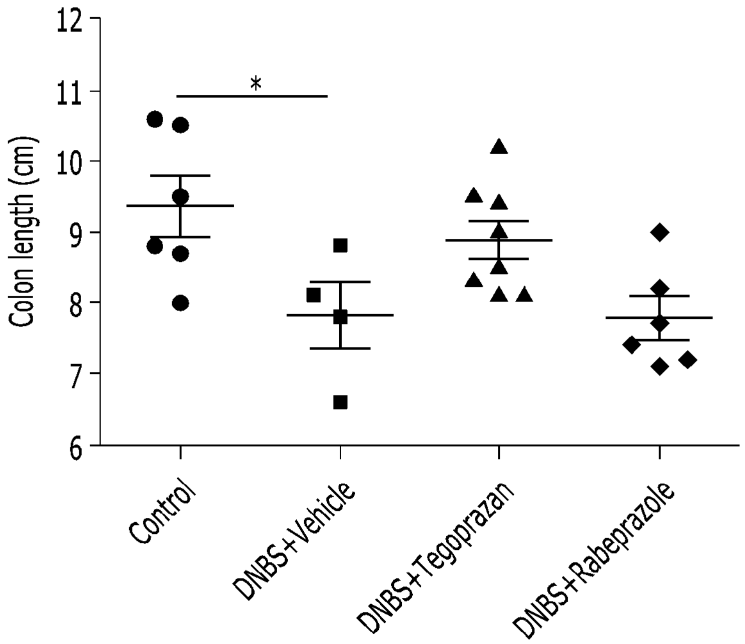
[Fig. 11]
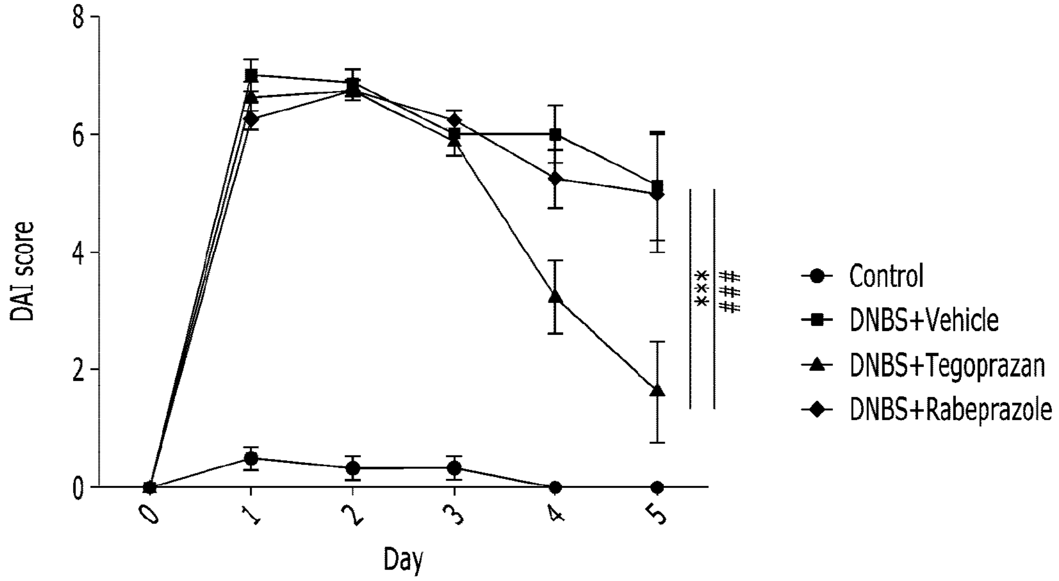

[Fig. 12]
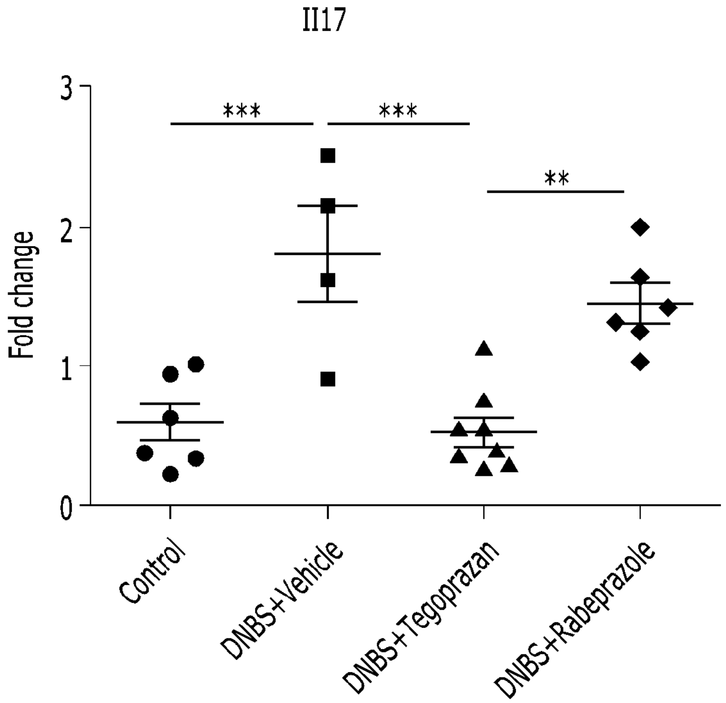

[Fig. 13]
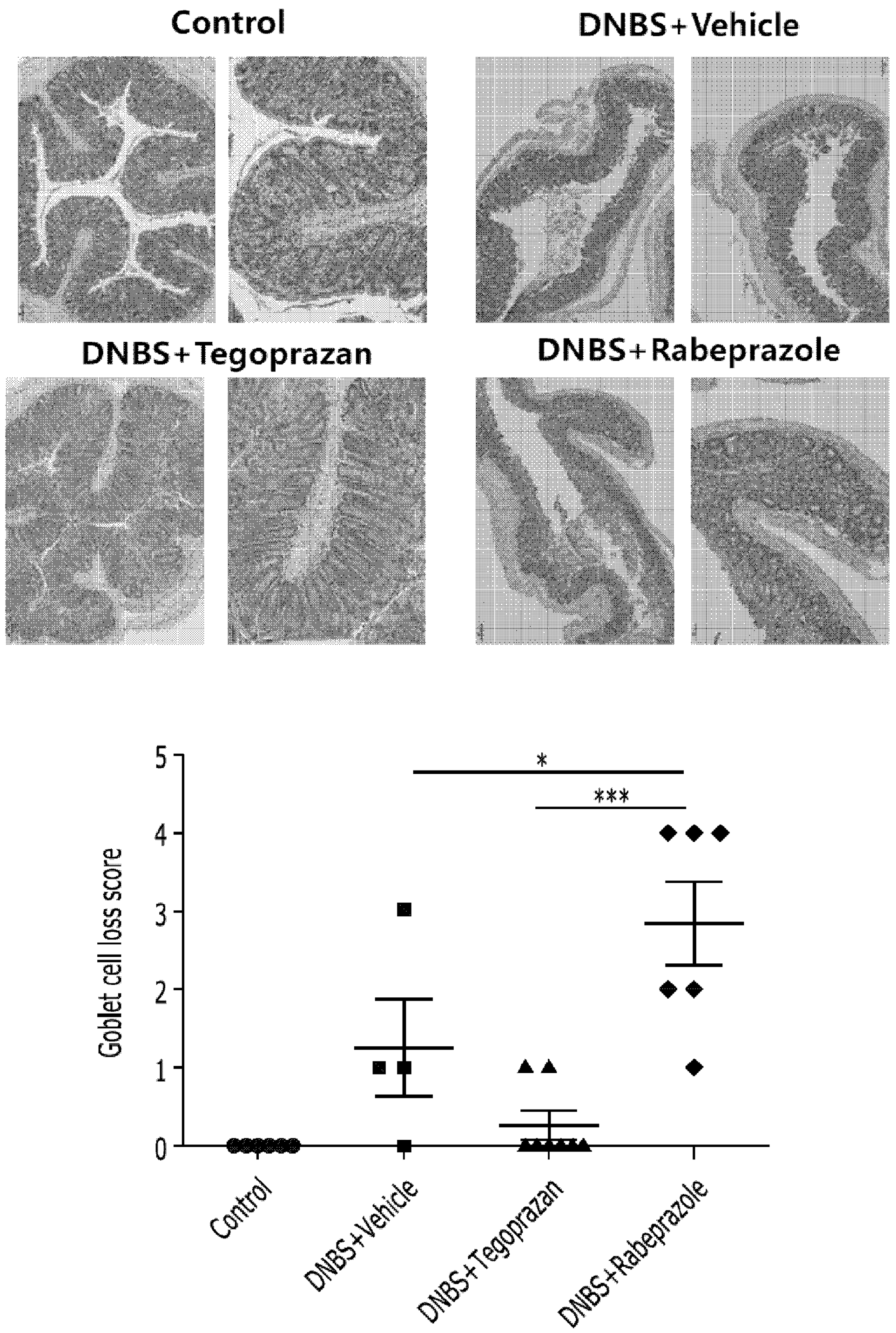

[Fig. 14]
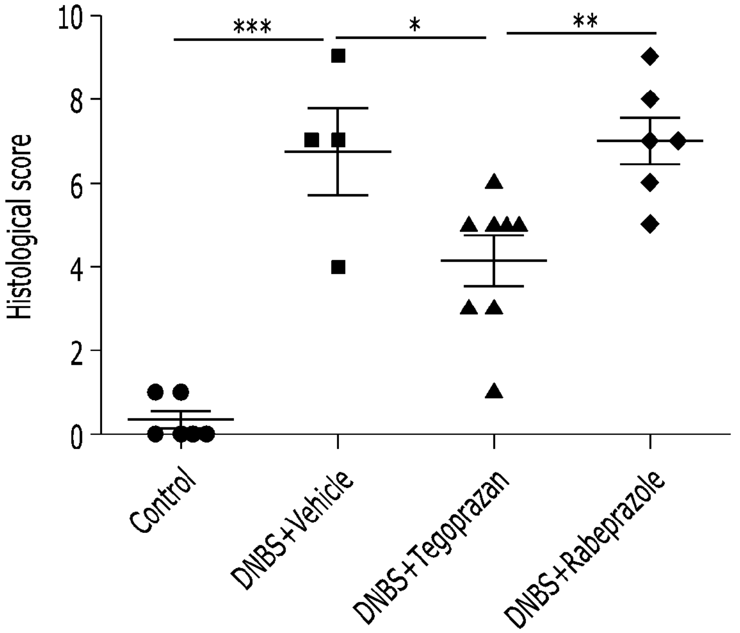
[Fig. 15]
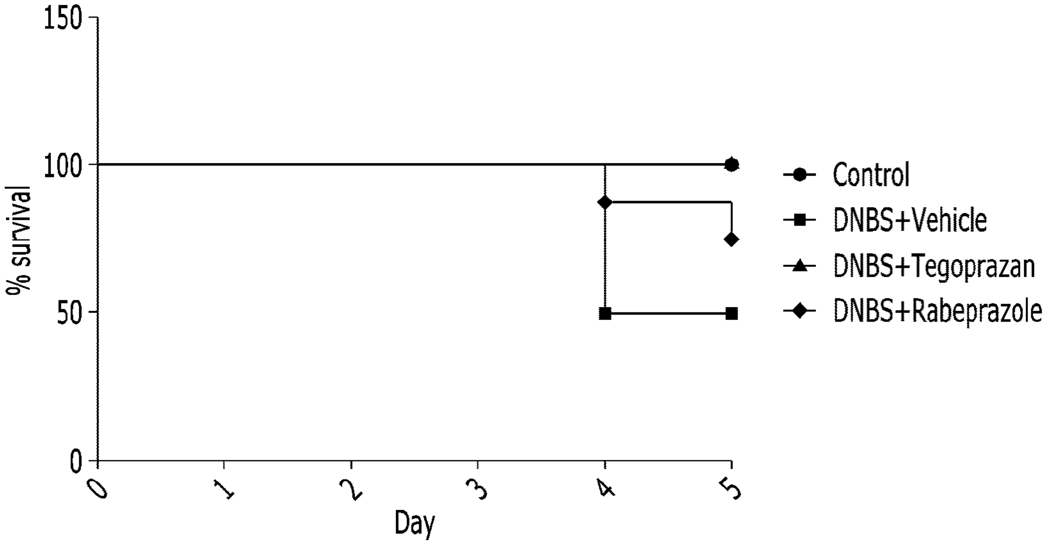

PHARMACEUTICAL COMPOSITION COMPRISING BENZIMIDAZOLE DERIVATIVE COMPOUND

TECHNICAL FIELD

The present invention relates to a pharmaceutical composition including a benzimidazole derivative compound as an effective ingredient and, more particularly, to a pharmaceutical composition for a novel use including tegoprazan, a pharmaceutically acceptable salt thereof, a hydrate or solvate thereof, or a mixture thereof as an effective ingredient.

BACKGROUND ART

Colitis is a disease in which inflammation occurs in the large intestine, and may be roughly classified into infectious colitis and non-infectious colitis depending on the cause of the disease, and may be also classified into acute colitis and chronic colitis depending on the duration of the disease. Colitis includes not only inflammatory bowel disease (IBD), but also irritable bowel syndrome (IBS), etc.

Inflammatory bowel disease is a chronic inflammatory disease caused by a dys-regulated immune response, genetic susceptibility, environmental factors or the like. Inflammatory bowel disease is classified into ulcerative colitis and Crohn's disease, which are clinically similar to, but different from each other in terms of histological findings and in endoscopic and immunological aspects. With regard to the cause of the disease, an abnormal immune response to intestinal antigens is presumed to be one of the causes. Inflammatory bowel disease is a complicated and multifactorial disease and a representative intractable disease that is difficult to be treated without an effective remedy since the exact cause has not been identified yet.

It is reported that pro-inflammatory cytokines such as IL-β, TNF-α, etc., are increased in the colonic mucosa and serum of patients with inflammatory bowel disease and such increase plays an important role in sustaining and amplifying the inflammatory responses of the mucous membranes. Studies on the factors involved in the production and activation of the cytokines play an important role in the pathophysiology and treatment of inflammatory bowel disease.

To date, immunosuppressants, such as sulfasalazine, corticosteroids and azathioprine, biological therapies represented by anti-TNFα antibodies, etc., have been used as treatment for inflammatory bowel disease. However, there is a problem in that side effects related to these drugs occur during a long treatment period and a recurrence rate is also high. Thus, there is a need to develop a therapeutic agent for inflammatory bowel disease that exhibits a rapid effect on inflammatory bowel disease with less side effects.

Meanwhile, tegoprazan has drawn much attention as a novel drug which compensates for disadvantages such as a slow expression of medicinal effect, a failed inhibition of acid secretion at night, etc., despite the strong gastric acid secretion inhibitory ability of an existing proton pump inhibitor (PPI). Tegoprazan is a compound named as (S)-4-(5,7-difluorochroman-4-yloxy)-N,N,2-trimethyl-1H-benzo[d]imidazole-6-carbox amide (or 7-{[(4S)-5,7-difluoro-3,4-dihydro-2H-chromen-4-yl]oxy}-N,N,2-trimethyl-1H-benzim idazole-5-carboxamide) and is a potassium-competitive acid blocker (P-CAB) having therapeutic potential for gastroesophageal reflux disease (GERD) by reversibly inhibiting gastric $H^+/K^+$-ATPase.

The present inventors have confirmed that tegoprazan inhibits a length of the large intestine from being shortened, significantly ameliorates a disease activity index, inhibits the production of TNF-α, IL-6, IL-17 and IL-1β, and expresses Muc2 mRNA. Accordingly, it has been confirmed that tegoprazan can be useful as an effective ingredient of a composition for preventing or treating colitis, thereby completing the present invention.

DISCLOSURE OF INVENTION

Technical Problem

The present invention is to provide a pharmaceutical composition which includes tegoprazan, which is a benzimidazole derivative compound, as an effective ingredient for treating or preventing diseases for which an effect of treatment or prevention has not been identified in the prior art.

Solution to Problem

The present invention provides a pharmaceutical composition for preventing or treating colitis, which includes tegoprazan, which is a benzimidazole derivative compound represented by the following chemical formula 1, a pharmaceutically acceptable salt thereof, a hydrate or solvate thereof, or a mixture thereof, as an effective ingredient.

[Chemical Formula 1]

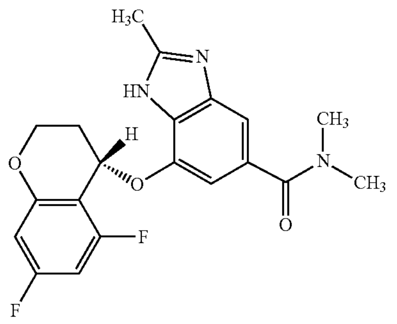

The present invention provides a method for preventing or treating colitis, the method comprising administering a therapeutically effective amount of a compound represented by a chemical formula 1, a pharmaceutically acceptable salt thereof, a hydrate or solvate thereof, or a mixture thereof into an individual.

The present invention provides a use of a compound represented by the chemical formula 1, a pharmaceutically acceptable salt thereof, a hydrate or solvate thereof, or a mixture thereof for preventing or treating colitis.

The present invention provides a use of a compound represented by the chemical formula 1, a pharmaceutically acceptable salt thereof, a hydrate or solvate thereof, or a mixture thereof in preparation of a medicament for treating colitis.

In the present invention, "colitis" may refer to a state in which inflammation occurs to the large intestine or the colon due to bacterial infection, pathological fermentation of intestinal content, or the like, and may be involved in a concept including infectious colitis and non-infectious colitis. Specific examples of colitis that can be prevented or treated through the pharmaceutical composition according to the present invention may include inflammatory bowel disease (IBD), irritable bowel syndrome (IBS) or the like.

In addition, colitis that can be prevented or treated through the pharmaceutical composition according to the present invention may include both acute colitis and chronic colitis. The acute colitis may be an inflammation that acutely occurs, and mucous membranes may be damaged by the inflammation, mainly leading to symptoms of mucous diarrhea or fresh blood. In the present invention, acute colitis may include not only general acute infectious colitis, but also acute pseudomembranous colitis and acute ulcerative colitis.

In the present invention, "inflammatory bowel disease" may mean chronic inflammation which occurs to the bowels without any known cause, and may usually refer to ulcerative colitis and Crohn's disease, which are idiopathic inflammatory bowel diseases, but may also include intestinal Behcet's disease which is relatively common in Korea. In addition, inflammatory bowel disease may be defined as a collective term for inflammatory diseases that occur to all intestines, such as infectious enteritis including bacterial, viral, amoebic, tuberculous enteritis and the like, ischemic bowel disease, radiation enteritis, etc.

In the present invention, an expression that a subject's colitis has been treated or prevented may refer to preventing or delaying the occurrence of clinical symptoms that develop the disease, stopping or decreasing the occurrence of the disease, or alleviating the disease in the subject who may have already had the disease but has not yet experienced or shown any clinical signs.

As a result of observing a preventive and therapeutic effect on colitis in animal models of colitis induced by dextran sodium sulfate (DSS) and 2,4-dinitrobenzenesulfonic acid hydrate (DNBS), it has been confirmed that tegoprazan minimizes a change in body weight of the animal model, minimizes a change in the length of the large intestine, or inhibits a decrease in the length of the large intestine, and shows an excellent ameliorating effect even through the disease activity index (DAI), which shows a decrease in body weight, the degree of bloody stool, and stool viscosity.

Inflammatory cytokines, such as TNF-α, IL-6, etc. may cause intestinal mucosa inflammation or ulceration, leading to intestinal mucosa dysfunction and damage. TNF-α may induce neutrophils to an affected site at the beginning of inflammatory responses, and may be a factor that causes and aggravates an acute inflammatory response. IL-6 is a representative inflammatory cytokine and plays an important role in the occurrence and progress of acute or chronic inflammatory disease while being synthesized and secreted by various factors. It has been confirmed that tegoprazan of the present invention inhibits the production/expression of TNF-α, IL-6, IL-17 and IL-1β which are inflammatory cytokines in colonic tissues.

In addition, it has been confirmed that tegoprazan expresses Muc2 mRNA, which is an mRNA of mucin protein essential for protecting epithelial cells.

Furthermore, in the animal model with DSS-induced colitis, it has been confirmed that tegoprazan decreases the expression of KCNJ1 mRNA which is increased by DSS.

Moreover, it has been confirmed that tegoprazan has an effect of alleviating the permeability of the large intestine.

In the present invention, the subject may refer to animals, and may be typically mammals, on which treatment using a pharmaceutical composition of the present invention may provide a beneficial effect. A preferable example of such subjects may include primates like humans. In addition, the subjects may include all the subjects having a symptom of colitis or having a risk of developing the symptom.

In embodiments of the present invention, the pharmaceutically acceptable salt may refer to the salts formed with any inorganic acid, organic acid or base, which neither cause a serious stimulus to the subject dosed therewith, nor do damage to biological activity and physical property of the tegoprazan. As salts, it may be possible to use the salts conventionally used in the art, such as acid-addition salts formed with pharmaceutically acceptable free acid. The pharmaceutically acceptable salts may be selected particularly from the group consisting of pidolate salt, acetate salt, adipate salt, aspartate salt, benzoate salt, besylate salt, bicarbonate salt/carbonate salt, bisulfate salt/sulfate salt, borate salt, camsylate salt, citrate salt, cyclamate salt, edisylate salt, esylate salt, formate salt, fumarate salt, gluceptate salt, gluconate salt, glucuronate salt, hexafluorophosphate salt, hibenzate salt, hydrochloride salt/chloride salt, hydrobromide salt/bromide salt, hydroiodide salt/iodide salt, isethionate salt, lactate salt, malate salt, maleate salt, malonate salt, mesylate salt, methylsulphate salt, naphthylate salt, 2-napsylate salt, nicotinate salt, nitrate salt, orotate salt, palmitate salt, pamoate salt, phosphate salt/hydrogen phosphate salt/dihydrogen phosphate salt, pyroglutamate salt, saccharate salt, stearate salt, succinate salt, tannate salt, tartrate salt, tosylate salt, trifluoroacetate salt and xinofoate salt, but are not limited thereto. Any salts may be used without limitation, as long as they may conventionally show the pharmacological activity of tegoprazan.

In embodiments of the present invention, hydrate of tegoprazan may mean that tegoprazan or a pharmaceutically acceptable salt thereof and water are bound by a non-covalent intermolecular force, and may include a stoichiometric or non-stoichiometric amount of water.

In embodiments of the present invention, solvate of tegoprazan may mean that tegoprazan or a pharmaceutically acceptable salt thereof and a solvent other than water are bound by an intermolecular force, and may include the solvent in a stoichiometric or non-stoichiometric amount.

According to the present invention, the pharmaceutical composition for preventing or treating colitis may further include pharmaceutically acceptable additives, conventionally used appropriate carriers, excipients, disintegrants, binders, glidants or diluents.

The "pharmaceutically acceptable additives" may include carriers, excipients, disintegrants, binders, glidants or diluents, which neither irritate organisms nor inhibit the biological activity and properties of an injected compound. The types of additives usable in the present invention are not particularly limited, and any additives may be used, as long as they are conventionally used in the art and pharmaceutically acceptable. A non-limiting example of the additives may include mannitol, microcrystalline cellulose, croscarmellose sodium, hydroxypropyl cellulose, colloidal silicon dioxide, magnesium stearate or mixtures thereof. Also, such additives may be used with the addition of other conventional additives, such as antioxidants, buffer solutions, bacteriostatic agents and/or the like, if necessary.

According to the present invention, the pharmaceutical composition for preventing or treating colitis may be formulated into a dosage form for oral administration, and may be formulated into a dosage form, such as tablets, troches, lozenges, water-soluble or oil suspensions, prepared powders or granules, emulsions, hard or soft capsules, syrup, elixirs or the like.

In addition, the pharmaceutical composition of the present invention may be parenterally administered. The parenteral administration may be performed by means of subcutaneous injection, intravenous injection, intramuscular injection or intrathoracic injection method. To formulate into the dosage form for parenteral administration, the composition may be prepared into solution by being mixed in water with stabilizers or buffer agents, and then may be prepared again into a unit form for administration of ampoule or vial.

A dosage of the pharmaceutical composition according to the present invention may need to be a pharmaceutically effective amount. The "pharmaceutically effective amount" may mean an amount enough to prevent or treat diseases at a reasonable benefit/risk ratio applicable to medical treatment, and a level of effective dose may be variously selected by those skilled in the art according to factors such as a formulation method, a patient's condition, weight, gender and age, a degree of disease, a drug form, an administration route and period, an excretion rate, reaction sensitivity, etc. The effective amount may vary depending on a route of treatment, a use of excipients and a possibility of being used with other drugs, as recognized by those skilled in the art.

The present invention may provide a use of a pharmaceutical composition including tegoprazan or a pharmaceutically acceptable salt thereof as an effective ingredient for preventing or treating colitis.

The present invention may provide a use of a pharmaceutical composition including tegoprazan or a pharmaceutically acceptable salt thereof as an effective ingredient for producing a drug for the prevention or treatment of colitis.

The present invention may provide a method for preventing or treating colitis, including administering a pharmaceutically effective amount of a pharmaceutical composition including tegoprazan or a pharmaceutically acceptable salt thereof as an effective ingredient.

Advantageous Effects of Invention

Tegoprazan, which is an effective ingredient of a pharmaceutical composition for preventing or treating colitis according to the present invention, can have an effect of reducing an activity and expression of inflammatory activation markers and alleviating a disease activity index of colitis, and thus can be useful as an effective ingredient of the pharmaceutical composition for preventing and treating colitis.

BRIEF DESCRIPTION OF DRAWINGS

FIG. 1 is a graph showing the rate of change (%) in mouse body weight for nine days in each of the four mouse groups: a normal control group (control), a group with induced colitis (DSS+Veh), a group dosed with tegoprazan (DSS+Tegoprazan), and a group dosed with a control drug (DSS+Rabeprazole), with regard to the model of colitis induced by DSS.

FIG. 2 is a graph showing the length of the large intestine of the four mouse groups, with regard to the model of colitis induced by DSS.

FIG. 3 is a graph showing the disease activity index (DAI) score of the four mouse groups, with regard to the model of colitis induced by DSS.

FIG. 4 is a graph showing the fold change in expression of KCNJ1 mRNA of the four mouse groups, with regard to the model of colitis induced by DSS.

FIG. 5 is a graph showing the fold change value in expression of mRNA of TNF-α, IL-6, IL-1β and Muc2 in colonic tissues of the four mouse groups, with regard to the model of colitis induced by DSS.

FIG. 6 is pictures of analyzed colonic tissues of the four mouse groups stained with periodic acid-Schiff (PAS) and a graph showing the score of goblet cell loss, with regard to the model of colitis induced by DSS.

FIG. 7 is a graph showing the scored degree of damage to colonic tissues of the four mouse groups, with regard to the model of colitis induced by DSS.

FIG. 8 is a graph showing the results of evaluating intestinal permeability properties by inflammation of the four mouse groups, with regard to the model of colitis induced by DSS.

FIG. 9 is a graph showing the rate of change (%) in mouse body weight for five days in each of the four mouse groups: a normal control group (control), a group with induced colitis (DNBS+Vehicle), a group dosed with tegoprazan (DNBS+Tegoprazan), and a group dosed with a control drug (DNBS+Rabeprazole), with regard to the model of colitis induced by DNBS.

FIG. 10 is a graph showing the length of the large intestine of the four mouse groups, with regard to the model of colitis induced by DNBS.

FIG. 11 is a graph showing the disease activity index (DAI) score of the four mouse groups, with regard to the model with colitis induced by DNBS.

FIG. 12 is a graph showing the fold change value in expression of mRNA of IL-17 in colonic tissues of the four mouse groups, with regard to the model of colitis induced by DNBS.

FIG. 13 is pictures of analyzed colonic tissues of the four mouse groups stained with periodic acid-Schiff (PAS) and a graph showing the score of goblet cell loss, with regard to the model of colitis induced by DNBS.

FIG. 14 is a graph showing the scored degree of damage to colonic tissues of the four mouse groups, with regard to the model of colitis induced by DSS.

FIG. 15 is the results of an experiment evaluating the survival rate of the model of DNBS-induced colitis.

MODE FOR THE INVENTION

Hereinafter, the present invention will be described in more detail through exemplary embodiments. These exemplary embodiments are provided only for the purpose of illustrating the present invention in more detail, and thus the scope of the present invention is not limited thereto.

Mouse Model of Colitis Using DSS

C57BL/6 male mice, which were eight weeks old (24.0 g), were purchased from Orient Bio, acclimated to the laboratory environment (temperature of 21±2° C. and humidity of 50±10%) for one week with a full access to feed and water, and used in an experiment.

The mice were divided into a normal control group (Control, n=6), a group with induced colitis (DSS+Veh, n=8), a group dosed with tegoprazan (DSS+Tegoprazan, n=8), and a group dosed with a control drug (DSS+Rabeprazole, n=8), and the experiment was performed.

To induce colitis, DSS (MPbio product, catalog No. 0216011080) was used.

The group with induced colitis (DSS+Veh) was dosed with 2.0% DSS in drinking water for consecutive five days, was suspended from 2.0% DSS administration from the 5th day, and was orally dosed with 0.5% (w/v) methylcellulose aqueous solution twice a day for three days until the 8th day.

The group dosed with tegoprazan (DSS+Tegoprazan) was orally dosed with tegoprazan (7-{[(4S)-5,7-difluoro-3,4-dihydro-2H-chromen-4-yl]oxy}-N,N,2-trimethyl-1H-benzi midazole-5-carboxamide), which was dissolved in 0.5% (w/v) methylcellulose aqueous solution, at a dose of 30 mg/kg/day twice a day for five days along with 2% DSS and drinking water. The group was suspended from 2.0% DSS administration from the 5th day, and was orally dosed with tegoprazan, which was dissolved in 0.5% (w/v) methylcellulose aqueous solution, twice a day for three days until the 8th day.

The group dosed with the control drug (DSS+Rabeprazole) was dosed with DSS and rabeprazole in substantially the same manner as the group dosed with tegoprazan, except for using rabeprazole instead of tegoprazan.

In the group dosed with tegoprazan and the group dosed with the control drug, the oral administration was performed twice a day by dividing the administration into morning/afternoon.

Mouse Model of Colitis Using DNBS

C57BL/6 male mice, which were eight weeks old (24.0 g), were purchased from Orient Bio, acclimated to the laboratory environment (temperature of 21±2° C. and humidity of 50±10%) for one week with a full access to feed and water, and used in an experiment.

The mice were divided into a normal control group (Control, n=6), a group with induced colitis (DNBS+Vehicle, n=8), a group dosed with tegoprazan (DNBS+Tegoprazan, n=8), and a group dosed with a control drug (DNBS+Rabeprazole, n=8), and the experiment was performed.

To induce colitis, DNBS (Sigma-Aldrich product, catalog No. 556971) was used. The mice were fasted from one day before being dosed with DNBS to remove the fecal waste in the intestine. The normal control group was dosed with 50% ethanol only by rectal route.

The administration of DNBS was done by dissolving 5 mg of DNBS in 50% ethanol and administering it by rectal route.

In the group dosed with tegoprazan (DNBS+Tegoprazan), the DNBS-administered mouse was orally dosed with tegoprazan (7-{[(4S)-5,7-Difluoro-3,4-dihydro-2H-chromen-4-yl]oxy}-N,N,2-trimethyl-1H-benzi midazole-5-carboxamide), which had been dissolved in 0.5% (w/v) methylcellulose aqueous solution, at a dose of 30 mg/kg/day twice a day for five days.

In the group dosed with the control drug (DNBS+Rabeprazole), the DNBS-administered mouse was dosed with rabeprazole in substantially the same manner as the group dosed with tegoprazan, except for using rabeprazole instead of tegoprazan.

In the group with induced colitis (DNBS+Vehicle), the DNBS-administered mouse was orally dosed with 0.5% (w/v) methylcellulose aqueous solution twice a day.

In the group dosed with tegoprazan, the group dosed with the control drug, and the group with induced colitis, the oral administration was performed twice a day by dividing the administration into morning/afternoon. After being dosed for four days, the mouse was sacrificed on the 5th day.

(1) Measurement and Result of Body Weight Changes (1-1) Mouse Model of Colitis Using DSS The body weight of each mouse was measured with regard to the normal control group, the group with induced colitis, the group dosed with tegoprazan, and the group dosed with the control drug. The body weight of the mouse was measured every morning from the start day of experiment (day 0), in which DSS was not administered, until the 9th day, and the body weight of the mouse, which was measured on the start day of experiment (day 0) without the administration of DSS, was converted into 100%. The results thereof were shown in FIG. 1.

Referring to FIG. 1, it can be confirmed that the normal control group showed a continuous increase in body weight from the 1st day to the 8th day. In contrast, it can be confirmed that the group with induced colitis, the group dosed with tegoprazan, and the group dosed with the control drug all showed no significant change in body weight until the 5th day, but the body weight was decreased from the 6th day.

On the 9th day on which the mouse was sacrificed, it can be confirmed that the group with induced colitis showed a decrease of about 21% in body weight and the group dosed with the control drug showed a rather more decrease of about 23% in body weight than that of the group with induced colitis, while the group dosed with tegoprazan showed a decrease of just about 14% in body weight.

In FIG. 1,  and * indicate a significant difference ($P<0.01$ and $P<0.001$) between the group with induced colitis and the group dosed with tegoprazan, respectively, and ### indicates a significant difference ($P<0.001$) between the group dosed with tegoprazan and the group dosed with the control drug.

(1-2) Mouse Model of Colitis Using DNBS

The body weight of each mouse in the normal control group, the group with induced colitis, the group dosed with tegoprazan, and the group dosed with the control drug was measured. The body weight of the mouse was measured every morning from the start day of experiment before administration of DNBS (day 0) to the 5th day, and the body weight of the mouse before administration of DNBS on day 0 was converted into 100%. In the case of the mouse sacrificed before the end of experiment, the weight of the mouse measured the day before sacrifice was included in the data as of the last day of experiment and converted (refer to FIG. 15 for survival period and survival rate). The results thereof were shown in FIG. 9.

Referring to FIG. 9, the normal control group showed a continuous increase in body weight, and the group with induced colitis, the group dosed with tegoprazan, and the group dosed with the control drug all showed a significant decrease in body weight until the 3rd day. The group dosed with tegoprazan showed an increase in body weight from the 4th day, and the body weight thereof increased and reached about 105% on the 5th day on which the mouse was sacrificed, confirming a recovery from body weight loss due to colitis. In contrast, the body weight of the group with induced colitis and the group dosed with the control drug reached 88% and 89%, respectively, confirming no recovery from body weight loss occurred after administration of DNBS.

In FIG. 9, *** indicates a significant difference ($P<0.001$) between the group with induced colitis and the group dosed with tegoprazan, and ### indicates a significant difference ($P<0.001$) between the group dosed with tegoprazan and the group dosed with the control drug.

(2) Measurement and Result of Changes in Length of Large Intestine (2-1) Mouse Model of Colitis Using DSS On the 9th day after an initial administration of 2% DSS solution, the mouse was sacrificed and the colon was removed therefrom to measure the length of the removed large intestine. The results thereof were shown in FIG. 2. (In FIG. 2, * indicates $P<0.05$ and ** indicates $P<0.01$.)

Referring to FIG. 2, it can be confirmed that the group with induced colitis showed a significant decrease (about 80%) in the length of the large intestine compared to the normal control group. Accordingly, it can be confirmed that colitis was induced by DSS. In addition, it can be confirmed that the group dosed with the control drug showed a decrease in the length of the large intestine similarly to the group with induced colitis.

In contrast, it can be confirmed that the group dosed with tegoprazan showed a rather increase in the length of the large intestine or no difference from the normal control group, suggesting that tegoprazan minimizes a change in the length of the large intestine or inhibits a decrease thereof, which is caused by colitis.

(2-2) Mouse Model of Colitis Using DNBS

On the 5th day after an initial administration of DNBS, the mouse was sacrificed, and the colon was removed therefrom to measure the length of the removed large intestine. The results thereof were shown in FIG. 10. (In FIG. 10, * indicates P<0.05.)

Referring to FIG. 10, it can be confirmed that the group with induced colitis showed a significant decrease (about 87%) in the length of the large intestine compared to the normal control group. Accordingly, it can be confirmed that colitis was induced by DNBS. In contrast, it can be confirmed that the group dosed with tegoprazan showed no difference in the length of the large intestine from the normal control group, suggesting that tegoprazan maintains the length of the large intestine, minimizes changes therein, or inhibits a decrease thereof, which is caused by colitis.

(3) Measurement and Evaluation of Disease Activity Index (DAI)

As DAI, a change in body weight, bloody stool and stool viscosity were measured every morning, and scored according to the following table 1.

TABLE 1

| Score | Weight loss | Bloody stool | Stool viscosity |
|---|---|---|---|
| 0 | (None) | Normal | Normal |
| 1 | More than 1% and 5% or less | Red bloody stool | Loose |
| 2 | More than 5% and 10% or less | Dark red bloody stool | Very loose |
| 3 | More than 10% and 20% or less | Serious blooding | Diarrhea |
| 4 | More than 20% | — | — |

The results thereof were shown in FIG. 3 and FIG. 11. (In relation to the animal model of colitis using DNBS, in the case of the mouse sacrificed before the end of experiment, the DAI score of the mouse measured the day before sacrifice was included in the data as of the last day of experiment and converted (refer to FIG. 15 for survival period and survival rate).)

In FIG. 3 and FIG. 11,  and * indicate a significant difference (P<0.01 and P<0.001) between the group with induced colitis and the group dosed with tegoprazan respectively, and # and ### indicate a significant difference (P<0.05 and P<0.001) between the group dosed with tegoprazan and the group dosed with the control drug, respectively.

(3-1) Mouse Model of Colitis Using DSS

Referring to FIG. 3, it can be confirmed that the group with induced colitis started to show red bloody stool from the 3rd day with an increase in the DAI score, and showed a big difference compared to previous days on the 6th day, which was the next day after the DSS administration was suspended to make a measurement, as well as the 9th day on which the mouse was sacrificed.

In the DAI score, it can be confirmed that the group dosed with tegoprazan took a turn for the better compared to the group with induced colitis, and the group with induced colitis and the group dosed with the control drug showed a significant difference on the 6th and 9th days compared to the group dosed with tegoprazan. It can be confirmed that the group dosed with the control drug showed results very similar to those of the group with induced colitis without any difference.

(3-2) Mouse Model of Colitis Using DNBS

Referring to FIG. 11 about the DAI score, DAI increased in all groups due to administration of DNBS, but in the case of the group dosed with tegoprazan, DAI drastically decreased from the 4th day, showing a significant difference from the group with induced colitis. In contrast, the group dosed with the control drug showed no big difference from the group with induced colitis. Accordingly, the effect of tegoprazan on alleviating colitis can be confirmed.

(4) Confirmation and Result of JCNJ1 mRNA Expression in Colonic Tissues

In the mouse model of colitis using DSS, the difference in expression of KCNJ1 mRNA was measured by using a real-time PCR. The results thereof were shown in FIG. 4. (In FIG. 4, ** indicates P<0.01.)

Referring to FIG. 4, it can be confirmed that the group with induced colitis showed a significant increase in expression of KCNJ1 mRNA compared to the normal control group, while the group dosed with tegoprazan showed a significant decrease in expression of KCNJ1 mRNA.

(5) Confirmation and Result of mRNA Expression of Inflammatory Cytokines in Colonic Tissues (5-1) Mouse Model of Colitis Using DSS In the mouse model of colitis using DSS, the level of mRNA expression of IL-1p, IL-6, Muc 2 and TNF-α was evaluated by using a real-time PCR. The results thereof were shown in FIG. 5. (In FIG. 5, * indicates P<0.05,  indicates P<0.01, and * indicates P<0.001.)

Referring to FIG. 5, it can be confirmed that the group dosed with tegoprazan showed a statistically significant decrease in mRNA expression of TNF-α and IL-6 compared to the group with induced colitis. In addition, it can be confirmed that the group dosed with tegoprazan also showed a statistically significant increase in mRNA expression of Muc2, which is essential for protecting epithelial cells.

(5-2) Mouse Model of Colitis Using DNBS

In the mouse model of colitis using DNBS, the level of mRNA expression of IL-17 was evaluated by using a real-time PCR. The results thereof were shown in FIG. 12. (In FIG. 12,  indicates P<0.01 and * indicates P<0.001.)

Referring to FIG. 12, it can be confirmed that the group dosed with tegoprazan showed a significant decrease in mRNA expression of IL-17, which is a pro-inflammatory cytokine, compared to the group with induced colitis. In addition, it was confirmed that mRNA expression of TNF-α and IL-6 tended to decrease in the group dosed with tegoprazan compared to the group with induced colitis.

(6) PAS Staining Analysis and Confirmation and Result of Damage to Colonic Tissues PAS staining analysis was performed on colonic tissues obtained from each of the animal models in which DSS and DNBS had been used, the goblet cell loss was scored according to the following table 2, and the degree of tissue damage was scored according to the following table 3.

TABLE 2

| Score | Rate of goblet cell loss |
|---|---|
| 0 | More than 0% and 10% or less |
| 1 | More than 10% and 20% or less |
| 2 | More than 21% and 35% or less |
| 3 | More than 36% and 50% or less |
| 4 | More than 51% |

TABLE 3

| Score | Degree of in-flammation | Scope of damage | Damage to crypt |
|---|---|---|---|
| 0 | Normal | Normal | Normal |
| 1 | Slight | Mucous membrane | ⅓ of base |
| 2 | Average | Mucous membrane and submucous | ⅔ of base |
| 3 | Serious | Transmural | No damage to surface epithelium only |
| 4 | — | — | Damage to whole crypt and epithelium |

The results thereof were shown in FIGS. 6, 7, 13 and 14. (In FIGS. 6, 7, 13 and 14, * indicates P<0.05,  indicates P<0.01, and * indicates P<0.001.)

(6-1) Mouse Model of Colitis Using DSS

Referring to FIG. 6, it can be confirmed that all the crypts were generally damaged and inflammatory cells were infiltrated throughout the colonic mucosa in the group with induced colitis.

In contrast, a partially intact crypt was observed in the group dosed with tegoprazan, and it can also be confirmed that goblet cells were also present compared to the group with induced colitis. The result of showing the presence of mucin-producing goblet cells is consistent with the result that the group dosed with tegoprazan showed an increase in the expression level of mRNA compared to the group with induced colitis in the experiment on mRNA expression of Muc2.

Referring to FIG. 7, it can be confirmed that the group dosed with tegoprazan showed a significant decrease in score (5.38±1.8 point) compared to the group with induced colitis (8.75±1.6 point). In contrast, the group dosed with the control drug (8.12±1.8 point) did not show a significant difference from the group with induced colitis in terms of the degree of tissue damage.

(6-2) Mouse Model of Colitis Using DNBS

Referring to FIG. 13, it can be confirmed that crypts were generally damaged and inflammatory cells were infiltrated throughout the colonic mucosa in the group with induced colitis. In contrast, a partially intact crypt was observed and the presence of mucin-producing goblet cells was confirmed in the group dosed with tegoprazan compared to the group with induced colitis.

In contrast, it was confirmed that crypt damage was not alleviated and the loss of goblet cells was higher in the group dosed with the control drug compared to the group with induced colitis.

Referring to FIG. 14, it can be confirmed that the group dosed with tegoprazan showed a significant decrease in score (4.1±16 point) compared to the group with induced colitis (6.8±2.1 point). In contrast, the group dosed with the control drug (7.0±1.4 point) did not show a significant difference from the group with induced colitis in terms of the degree of tissue damage.

(7) Experiment on FITC-Dextran Permeability

Four hours before the mouse was sacrificed in the mouse model of colitis using DSS, the mouse was orally dosed with FITC-dextran (80 mg/mL), after which cardiac puncture was performed to measure an FITC value in serum. Permeability (%) was converted based on the normal control group. The results thereof were shown in FIG. 8.

Referring to FIG. 8, the group with induced colitis showed an increase in an FITC value, suggesting that damage to the tight junction was induced by DSS. In addition, it can be confirmed that the damage to the tight junction was not alleviated in the group dosed with the control drug.

In contrast, it can be confirmed that the group dosed with tegoprazan showed a significant decrease in the damage to the tight junction.

(8) Experiment on Survival Rate of the Mouse Model of Colitis Using DNBS

The survival rate of the mouse model of DNBS-induced colitis was determined, and the results thereof were shown in FIG. 15.

Referring to FIG. 15, the survival rate of the group with induced colitis and the group dosed with the control drug as of day 5 was 50% and 75%, respectively. However, it was confirmed that all the subjects in the group dosed with tegoprazan survived until the last day of experiment, confirming that tegoprazan alleviates DNBS-induced colitis.

As a result of the experiment, it could be confirmed from the mouse model with DSS-induced or DNBS-induced colitis that the group dosed with tegoprazan showed a significant amelioration of symptoms in terms of length of the large intestine, weight loss and DAI score compared to the normal control group. In other words, in terms of the histological findings, some of intact crypt structures were observed in the group dosed with tegoprazan compared to the group with induced colitis which showed serious damage, and it might be possible to confirm a statistically significant effect of protecting mucosal damage even in the scored evaluation results. It was confirmed that tegoprazan shows an effect of significantly alleviating an intestinal permeability caused by inflammation, but an effect of alleviating inflammation in the large intestine could not be confirmed from the group dosed with the control drug, which is the PPI drug rabeprazole.

In summary, it can be confirmed that the pharmaceutical composition containincluding tegoprazan as an effective ingredient according to the present invention has an excellent effect on preventing and treating colitis.

While specific portions of the present invention have been described in detail above, it is apparent to those skilled in the art that such detailed descriptions are set forth to illustrate exemplary embodiments only, but are not construed to limit the scope of the present invention.

The invention claimed is:

1. A method of treating colitis comprising administering to a subject in need thereof a therapeutically effective amount of a compound of Chemical Formula 1, a pharmaceutically acceptable salt, hydrate, or solvate thereof, or a mixture thereof.

[Chemical Formula 1]

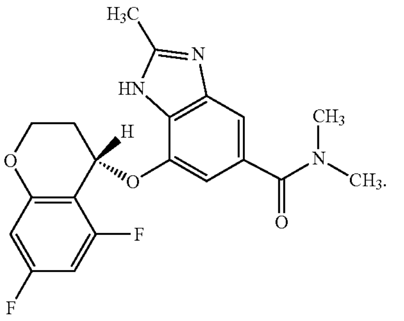

2. The method of claim 1, wherein the colitis is inflammatory bowel disease (IBD) or irritable bowel syndrome.

3. The method of claim 2, wherein the inflammatory bowel disease is Crohn's disease, ulcerative colitis, enteric Behcet's disease, infectious enteritis, ischemic bowel disease, or radiation enteritis.

4. The method of claim 1, wherein the colitis is acute colitis.

5. The method of claim 1, wherein the administration is oral administration.

6. The method of claim 1, further comprising inhibiting an expression of at least one inflammatory cytokine selected from the group consisting of TNF-α, IL-6, IL-17 and IL-1β.

7. A method of treating colitis comprising administering to a subject in need thereof a pharmaceutical composition comprising a therapeutically effective amount of a compound of Chemical Formula 1, a pharmaceutically acceptable salt, hydrate, or solvate thereof, or a mixture thereof:

[Chemical Formula 1]

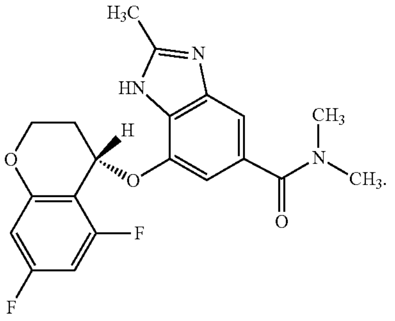

8. The method of claim 7, wherein the pharmaceutical composition is formulated for oral administration.

9. The method of claim 8, wherein the pharmaceutical composition is formulated as a tablet, troche, lozenge, water-soluble suspension, oil suspension, powder, granules, a hard capsule, a soft capsule, a syrup, or an elixir.

10. The method of claim 7, wherein the colitis is inflammatory bowel disease (IBD) or irritable bowel syndrome.

11. The method of claim 10, wherein the inflammatory bowel disease is Crohn's disease, ulcerative colitis, enteric Behcet's disease, infectious enteritis, ischemic bowel disease, or radiation enteritis.

12. The method of claim 7, wherein the colitis is acute colitis.

13. The method of claim 7, wherein the administration is oral administration.

14. The method of claim 7, further comprising inhibiting an expression of at least one inflammatory cytokine selected from the group consisting of TNF-α, IL-6, IL-17 and IL-1β.

* * * * *